(12) United States Patent
Lee et al.

(10) Patent No.: US 9,648,703 B2
(45) Date of Patent: May 9, 2017

(54) LIGHTING SYSTEM AND CONTROL METHOD THEREOF

(71) Applicant: LG ELECTRONICS INC., Seoul (KR)

(72) Inventors: Jaemyoung Lee, Seoul (KR); Inhwan Ra, Seoul (KR); Kyungtae Ro, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 14/683,267

(22) Filed: Apr. 10, 2015

(65) Prior Publication Data

US 2015/0296596 A1 Oct. 15, 2015

(30) Foreign Application Priority Data

Apr. 15, 2014 (KR) .................. 10-2014-0044974

(51) Int. Cl.
*H05B 37/02* (2006.01)
*H05B 33/08* (2006.01)
(Continued)

(52) U.S. Cl.
CPC ......... *H05B 37/0227* (2013.01); *A61M 21/02* (2013.01); *A61N 5/0618* (2013.01); *H05B 33/0842* (2013.01); *H05B 33/0872* (2013.01); *H05B 37/0272* (2013.01); *A61M 2021/0044* (2013.01); *A61M 2205/332* (2013.01); *A61M 2205/3303* (2013.01); *A61M 2205/3306* (2013.01); *A61M 2205/3375* (2013.01); *A61M 2205/505* (2013.01); *A61M 2210/0612* (2013.01); *A61M 2210/12* (2013.01);
(Continued)

(58) Field of Classification Search
CPC . A61B 2505/05; A61B 5/0022; A61B 5/0024; A61B 5/0026; A61B 5/0059; A61B 5/01; A61B 5/0205; A61B 5/1113; A61B 5/1118; A61B 5/14552; A61B 5/14556; A61B 5/1459; A61B 5/165; A61B 5/4809
See application file for complete search history.

(56) References Cited

U.S. PATENT DOCUMENTS

| 2007/0118026 A1 | 5/2007 | Kameyama et al. |
| 2012/0095357 A1 | 4/2012 | Tran |

(Continued)

FOREIGN PATENT DOCUMENTS

| JP | 2004-032540 | 1/2004 |
| JP | 2005-128976 | 5/2005 |

(Continued)

OTHER PUBLICATIONS

Korean Office Action dated Aug. 26, 2014 issued in Application No. 10-2014-0044974.

(Continued)

*Primary Examiner* — Monica C King
(74) *Attorney, Agent, or Firm* — KED & Associates LLP (57) ABSTRACT

A lighting device may include a communication unit for establishing a communication connection with a terminal, a light emitting unit (including one or more light emitting units), and a controller for receiving physical information from the communication unit and controlling the light emitting unit based on the physical information.

13 Claims, 8 Drawing Sheets

(51) Int. Cl.
*A61N 5/06* (2006.01)
*A61M 21/02* (2006.01)
*A61M 21/00* (2006.01)

(52) U.S. Cl.
CPC ..... *A61M 2230/06* (2013.01); *A61M 2230/30* (2013.01); *A61M 2230/63* (2013.01)

(56) References Cited

U.S. PATENT DOCUMENTS

| | | | |
|---|---|---|---|
| 2013/0134902 A1 | 5/2013 | Mahale et al. | |
| 2014/0266669 A1* | 9/2014 | Fadell | G05B 19/042 340/501 |
| 2015/0182130 A1* | 7/2015 | Utter, II | A61B 5/0205 600/483 |

FOREIGN PATENT DOCUMENTS

| | | |
|---|---|---|
| KR | 10-2004-0019380 | 3/2004 |
| KR | 10-0741839 B1 | 7/2007 |
| KR | 10-2009-0106149 A | 10/2009 |
| KR | 10-2011-0118783 | 11/2011 |
| KR | 10-2011-0133485 A | 12/2011 |
| KR | 10-1332944 B1 | 11/2013 |
| WO | WO 99/56262 A1 | 11/1999 |
| WO | WO 2010/079388 | 7/2010 |
| WO | WO 2012/146256 A1 | 11/2012 |
| WO | WO 2013/168034 A1 | 11/2013 |

OTHER PUBLICATIONS

Korean Office Action dated Feb. 16, 2015 issued in Application No. 10-2014-0044974.
Galaxy S5 Specifications, <URL: http://biz.newdaily.co.kr/news/article.html?no=10033737> (Original Korean website search page and English translation).
European Search Report dated Sep. 7, 2015 for Application No. 15163459.9.
Korean Office Action for Application 10-2014-0044974 dated Aug. 26, 2016.
Korean Office Action for Application 10-2014-0044974 dated Apr. 26, 2016 (full Korean text).
Using a Galaxy S5 . . . one hundred years old times health phone, Newdailybiz, [online], Apr. 1, 2014 (searching on Feb. 13, 2015) http://biz.newdaily.co.kr/news/article.html?no=10033737 (1 page) full Korean text).
Korean Office Action dated Dec. 22, 2016 issued in Application No. 10-2014-0044974.

* cited by examiner

LIGHTING SYSTEM AND CONTROL METHOD THEREOF

CROSS-REFERENCE TO RELATED APPLICATION

This application claims priority under 35 U.S.C. §119 from Korean Application No. 10-2014-0044974, filed Apr. 15, 2014, the subject matter of which is incorporated herein by reference.

BACKGROUND

1. Field

Embodiments may relate to a lighting system and a control method thereof that allow for lighting control based on physical information about a user.

2. Background

The lighting industry has continued to grow over the years. Research on light sources, light emission methods, operation methods, and/or efficiency improvement may be under way in connection with the lighting industry.

Light sources used mainly for illumination may include incandescent lamps, discharge lamps, and/or fluorescent lamps. Lighting using these light sources may be used for various purposes such as home lighting, landscape lighting, industrial lighting, etc. Resistant light sources, such as the incandescent lamps, may have problems of poor efficiency and heat generation. Discharge lamps may have problems of high price and high voltage. Fluorescent lamps may have environmental problems caused by use of mercury.

There may be a growing interest in light emitting diode (LED) lighting to solve drawbacks of light sources. The LED lighting may have advantages in efficiency, color variability, design flexibility, etc.

The light emitting diode is a semiconductor device that emits light when a voltage is applied thereto in a forward direction. The light emitting diode may have a long lifetime, a low power consumption, and electric, optical and physical characteristics suitable for mass production, to rapidly replace incandescent lamps and fluorescent lamps.

Smart technologies may get attention to provide a domestic ubiquitous environment where computing can occur anytime, in any place, and/or on any device by employing home networking and internet information home appliances based on wired/wireless communications and digital information appliances.

By combining smart technologies with lighting, technical advancements may be made in lighting control with a terminal when the lighting and the terminal are connected for communication. However, a user may have to enter a command on the terminal to control the lighting using the terminal.

SUMMARY OF THE INVENTION

Embodiments may provide a lighting system and a control method thereof that allow for lighting control based on physical information about a user.

An exemplary embodiment may be directed to a lighting device including: a communication unit that establishes a communication connection with a terminal having a sensing unit for sensing physical information about a user and receives the physical information sensed by the sensing unit; a light emitting unit (including one or more light emitting elements); and a controller for receiving the physical information from the communication unit and controlling the light emitting unit based on the physical information.

An exemplary embodiment may be directed to a lighting control method including: establishing a communication connection with a terminal having a sensing unit for sensing physical information about a user; receiving the physical information sensed by the sensing unit; and controlling a light emitting unit (including one or more light emitting elements) based on the physical information.

An exemplary embodiment may be directed to a terminal including: a sensing unit for sensing physical information about a user; a wireless communication unit for establishing a communication connection with a lighting device; and a terminal controller for controlling the transmission of the physical information sensed by the sensing unit to the lighting device via the wireless communication unit.

An exemplary embodiment may be directed to a lighting system including: a terminal including a sensing unit for sensing physical information about a user, a wireless communication unit for establishing a communication connection with a lighting device, and a terminal controller for controlling the transmission of the physical information sensed by the sensing unit to the lighting device via the wireless communication unit. The lighting device may include a communication unit for establishing a communication connection with the terminal, a light emitting unit (including one or more light emitting units), and a controller for receiving the physical information from the communication unit and controlling the light emitting unit based on the physical information.

A control method of a mobile terminal according to at least one exemplary embodiment may have the following:

A lighting system can find out user status information upon receipt of physical information about a user and control lighting based on the user status information. Accordingly, embodiments may have an active lighting control effect.

The lighting system may enable active lighting control corresponding to user status information without user's command. Accordingly, embodiments may increase user convenience.

BRIEF DESCRIPTION OF THE DRAWINGS

Embodiments may be described in detail with reference to the following drawings in which like reference numerals refer to like elements and wherein.

DETAILED DESCRIPTION

Embodiments may be described in detail with reference to the accompanying drawings.

In the following description, usage of suffixes such as 'module', 'unit' used for referring to elements is given merely to facilitate explanation of the present disclosure, without having any significant meaning by itself. Accordingly, both 'module' and 'unit' can be used in combination.

Figure 1:
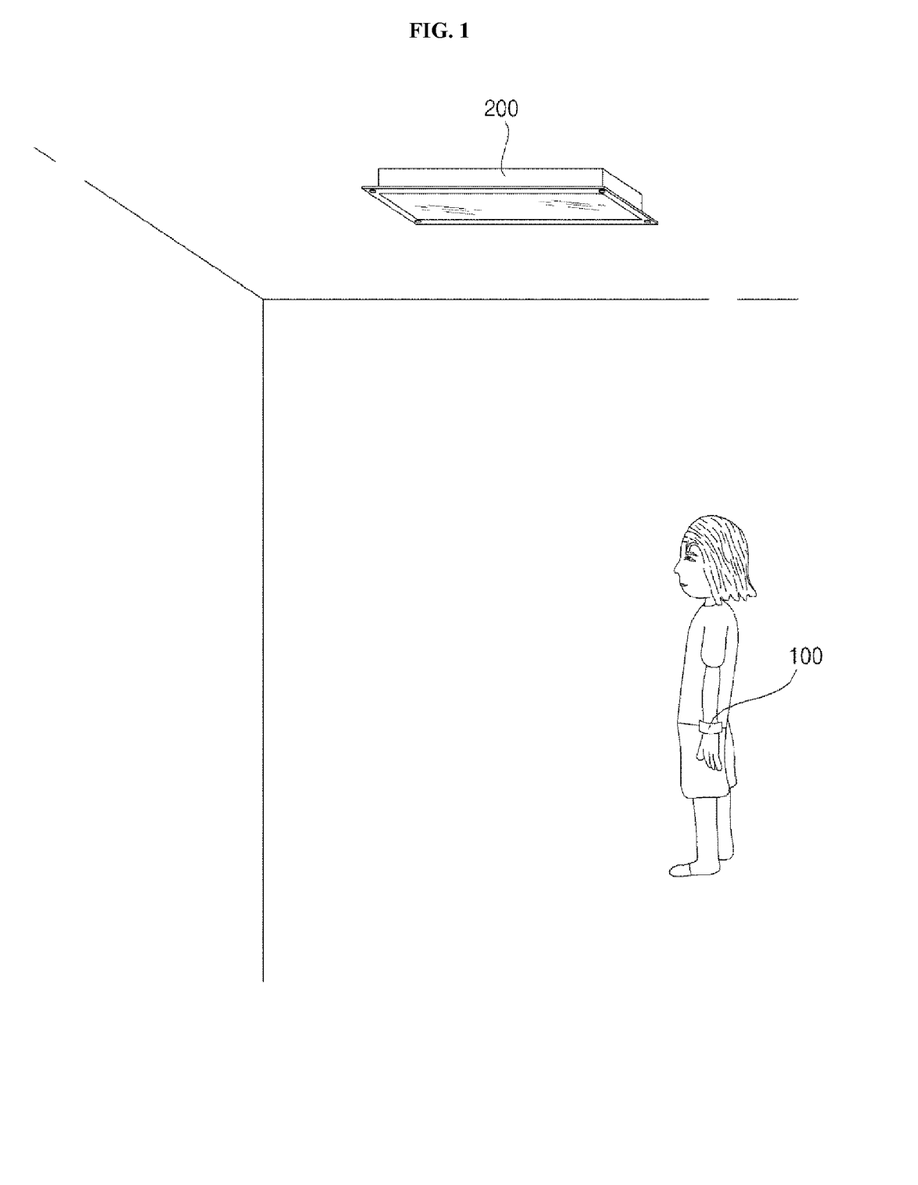
FIG. 1 is a view showing an environment where a lighting system according to an exemplary embodiment may be used.
Figure 2:
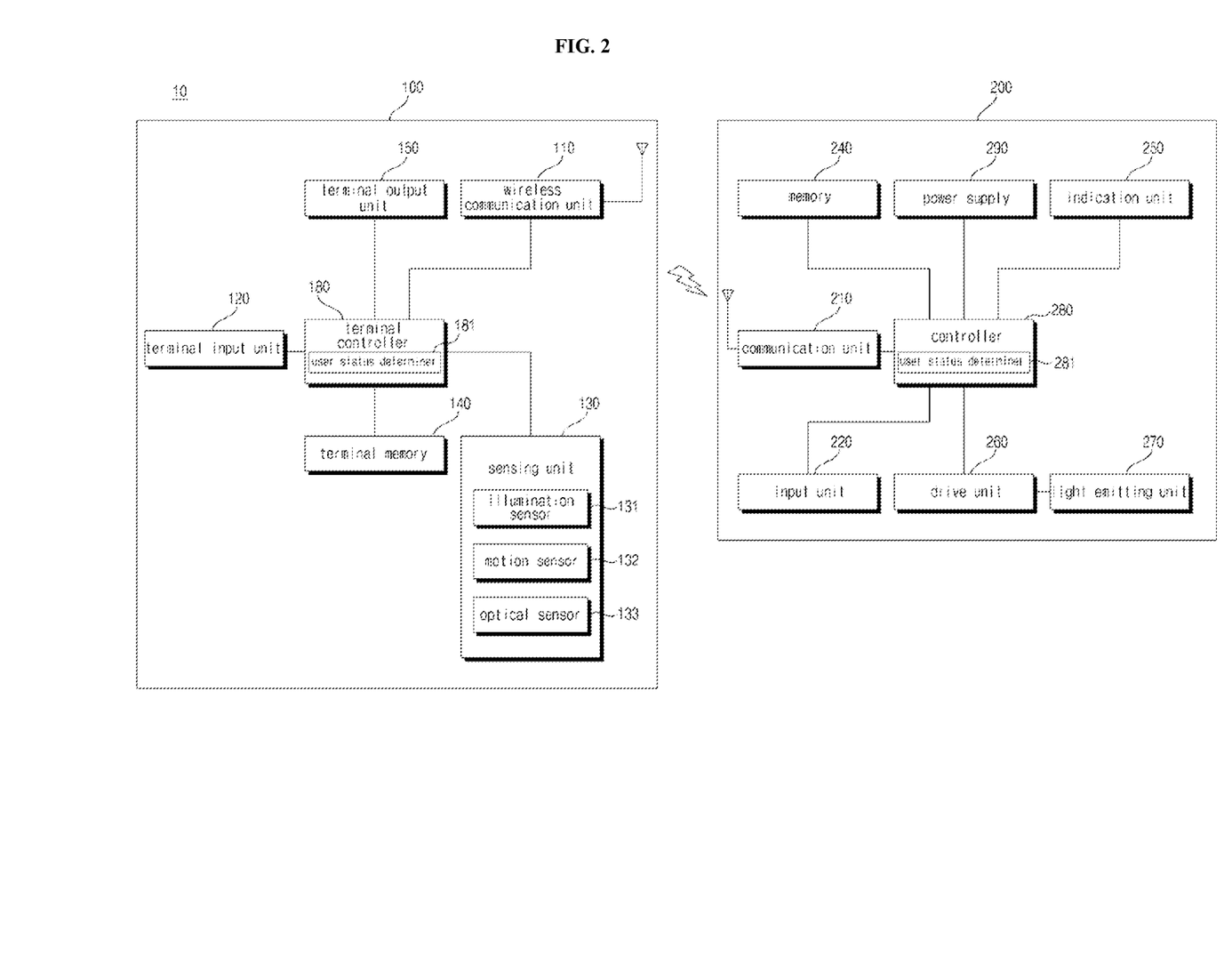
FIG. 2 is a block diagram showing the components of the lighting system according to the exemplary embodiment.

FIG. 1 is a view showing an environment where a lighting system according to an exemplary embodiment used. FIG. 2 is a block diagram showing components of the lighting system according to the exemplary embodiment. Other embodiments and configurations may also be provided.

Referring to FIGS. 1 and 2, embodiments may pertain to a lighting system that controls a light emitting unit 270 based on information sensed by a sensing unit 130 of a terminal 100 by communicating with the terminal 100. The lighting system may include one lighting device 200 according to an exemplary embodiment to be described with reference to the drawings. However, the lighting system may be applicable to a plurality of lighting devices.

The lighting system may include a terminal 100 and a lighting device 200.

This specification may be described, focusing on, but not limited to, a wearable device. The wearable device may refer to an electronic device that can be worn. However, the wearable device is not the type of electronic device that can be simply worn on the body, like an accessory, but an electronic device that enables communication with the user from a closest point to the user's body.

The terminal 100 may include a wireless communication unit 110, a terminal input unit 120, a sensing unit 130, a terminal memory 140, a terminal output unit 150, and a terminal controller 180.

The wireless communication unit 110 may include one or more modules that enable wireless communications between the terminal 100 and the lighting device 200 or between the terminal 100 and another terminal 100. The wireless communication unit 110 may include one or more modules that connect the terminal 100 to one or more communication networks.

The wireless communication unit 110 may communicate with the lighting device 200 over Bluetooth. Bluetooth may allow for communication at low power and may be set up at low cost. Accordingly, Bluetooth may be preferred for indoor short range communication between the terminal 100 and the lighting device 200.

The wireless communication unit 110 may use communication protocols such as Wi-Fi Direct, RFID (Radio Frequency Identification), IrDA (Infrared Data Association), UWB (Ultra Wideband), ZigBee, and NFC (Near Field Communication), as well as Bluetooth.

The wireless communication unit 110 may communicate with the lighting device 200, and transmit information sensed by the sensing unit 130 to the lighting device 200.

The terminal input unit 120 may include a camera or an image input unit for inputting an image signal, a microphone or an audio input unit for inputting an audio signal, and a user input unit (for example, a touch key or a mechanical key) for receiving information from the user. Audio data or image data collected by the terminal input unit 120 may be analyzed and processed into a user's control command.

The sensing unit 130 may include one or more sensors for sensing at least one of the following: information in the terminal 100, information on the environment surrounding the terminal 100, and user information.

For example, the sensing unit 130 may include at least one of the following: an illumination sensor 131, a motion sensor 132, an optical sensor 133 (e.g., camera), a touch sensor, a proximity sensor, an acceleration sensor, a magnetic sensor, a G-sensor, a gyroscope sensor, an RGB sensor, an IR (infrared) sensor, a finger scan sensor, an ultrasonic sensor, a microphone, a battery gauge, an environment sensor (e.g., barometer, hygrometer, thermometer, radiation sensor, thermal sensor, or gas sensor), and a chemical sensor (e.g., electronic nose, health-care sensor, or biometric sensor). A mobile terminal may use information sensed by at least two of these sensors in combination.

The illumination sensor 131 may sense the level of illumination of surrounding light in a certain space. The illumination sensor 131 may include an element whose resistance changes depending on intensity of the surrounding light. The illumination sensor 131 may calculate variations of voltage or current caused by variations in the resistance of the element.

The motion sensor 132 may include a location sensor or an acceleration sensor. The terminal 100 may measure an amount of exercise and calories the user burns by means of the location sensor or the acceleration sensor. That is, the terminal 100 is a wearable device, and when the user is wearing the wearable device and moving the body unit wearing it, the terminal 100 can measure the amount of exercise and calories the user burns by using the motion sensor 132.

The optical sensor 133 may sense the blood flow in the user's body. The terminal 100 can measure the heart rate and blood pressure of the user using the sensed blood flow. For example, if the terminal 100 is in the form of an earphone that is worn on the user's ear, the optical sensor 133 can measure the blood flow in the user's ear. In this example, the terminal controller 180 may measure the heart rate and blood pressure of the user using the sensed blood flow. In another example, if the terminal 100 is a glasses-type device configured to be worn on a human head, the optical sensor 133 can sense how much the user's pupil dilates. The optical sensor 133 can also sense whether the user's eyes are closed or not.

Human skin is normally transparent. When strong light is flashed on the skin, the light may shine through the skin. When the heart beats, skin transparency may change.

If the terminal 100 further includes a light emitting unit (e.g., LED device), the terminal 100 may flash strong light emitted from the light emitting unit on the user's skin. The optical sensor 133 senses a change in skin transparency with heart rate. The terminal controller 180 can measure the heart rate or pulse rate of the user using the amount of change in skin transparency.

The terminal memory 140 may store data that supports various functions of the terminal 100. The terminal memory 140 may store multiple application programs (or applications) that run on the terminal 100 and data and commands for operating the terminal 100. The terminal memory 140 may store blood flow, blood pressure, heart rate, pulse rate, or how much the pupil dilates, which are sensed by the sensing unit 130 or calculated by the terminal controller 180.

The terminal output unit 150 may be for producing output related to visual, auditory, and tactile senses. The wearable device output unit 150 may include at least one of a display, a sound output module, a haptic module, and a light output unit. The display may be implemented as a touch screen that forms an interlayer structure with a touch sensor or is integrated with it. The touch screen may function as the terminal input unit 120 that provides an input interface between the terminal 100 and the user, or may provide an output interface between the terminal 100 and the user.

The terminal controller 180 may control the overall operation of the terminal 100. The terminal controller 180 may process signals, data, information, etc. input or output through each of the components. The terminal controller 180 may provide proper information or function to the user or process them by running an application program stored in the terminal memory 140.

The terminal controller 180 may control at least some of the components. The terminal controller 180 may operate at least two of the components contained in the terminal 100 in combination, in order to run the application program.

The terminal controller 180 may include a user status determiner 181. The user status determiner 181 may determine the user's status based on physical information about the user received from the sensing unit 130. The user status determiner 181 can calculate blood pressure, heart rate, pulse rate, etc., based on a change in skin transparency with respect to the blood pressure or heart rate in a unit of the user's body sensed by the optical sensor 133.

For example, the heart rate or pulse rate of the user, which is determined based on the blood flow in a unit of the user's body sensed by the optical sensor 133, may be greater than or equal to a first reference value. The motion sensor 132 can sense that the terminal 100 is continuously moving. In this example, the user status determiner 181 may determine that the user is exercising. The first reference value may be a set value that is determined from a test.

For example, the heart rate or pulse rate of the user, which is determined based on the blood flow in a specific unit of the user's body sensed by the optical sensor 133, may be less than the first reference value and greater than or equal to a second reference value. The motion sensor 132 can sense that the terminal 100 is not continuously moving. In this example, the user status may determine 181 determines that the user is taking a rest. The first and second reference values are set values that are determined from a test.

For example, the heart rate or pulse rate of the user, which is determined based on the blood flow in a specific unit of the user's body sensed by the optical sensor 133, may be less than the second reference value. The motion sensor 132 can sense that the terminal 100 is not continuously moving. The optical sensor 133 may sense that the use's eyes are closed. In this example, the user status determiner 181 may determine that the user is sleeping. The second reference value may be a set value that is determined from a test.

The terminal controller 180 may transmit information sensed by the sensing unit 130 to the lighting device 200 via the wireless communication unit 110. Alternatively, the terminal controller 180 may transmit user status information determined by the user status determiner 181 to the lighting device 200 via the wireless communication unit 110.

The terminal controller 180 may be implemented using at least one of application specific integrated circuits (ASICs), digital signal processors (DSPs), digital signal processing devices (DSPDs), programmable logic devices (PLDs), field programmable gate arrays (FPGSs), processors, controllers, micro-controllers, microprocessors and electrical units for executing other functions.

The lighting device 200 may include a communication unit 210, an input unit 220, a memory 240, an indication unit 250, a drive unit 260, a light emitting unit 270, a controller 280, and a power supply 290.

The communication unit 210 may send and receive data by communicating with the terminal 100. The communication unit 210 may connect with the controller 280, and send and receive data to and from the terminal 100 in response to a control signal. The communication unit 210 may transmit the data received from the terminal 100 to the controller 280.

The wireless communication unit 210 may communicate with the terminal 100 over Bluetooth. The wireless communication unit 210 may use communication protocols such as Wi-Fi Direct, RFID (Radio Frequency Identification), IrDA (Infrared Data Association), UWB (Ultra Wideband), Zig-Bee, and NFC (Near Field Communication), as well as Bluetooth.

The communication unit 210 may include an RF (Radio Frequency) circuit. The communication unit 210 may send and receive RF signals (i.e., electromagnetic signals). The RF circuit may convert an electrical signal into an electromagnetic signal or vice versa, and communicate with the terminal 100 using the electromagnetic signal.

For example, the RF circuit may include an antenna system, an RF transceiver, one or more amplifiers, a tuner, one or more oscillators, a digital signal processor, a CODEC chipset, memory, etc. The RF circuit may include well-known circuitry for performing communication functions.

The communication unit 210 may receive information sensed by the sensing unit 130 by communicating with the terminal 100 having the sensing unit 130. For example, the communication unit 210 may receive physical information about the user from the terminal 100. The physical information may include blood flow, blood pressure, heart rate, pulse rate, and how much the pupil dilates.

Alternatively, the communication unit 210 may receive, from the terminal 100, information on the level of illumination in the surrounding environment sensed by the illumination sensor 131.

The input unit 220 may receive the brightness of the light emitting unit 270 which is selected by the user. The input unit 220 may be embedded in the lighting device 200. Alternatively, the input unit 220 may be configured separately from the lighting device 200. The input unit 220 may be connected to a remote controller either by wires or wirelessly, and receive user input. The input unit 220 may include a keypad, a dome switch, a touchpad (static pressure/capacitance), a jog wheel, a jog switch, and the like.

For example, if the input unit 220 is a jog wheel, the user may adjust the brightness of the lighting device 200 by turning the jog wheel. According to the user's selection, the input unit 220 may generate a brightness selection signal and output it to the controller 280. In this example, the user may choose to switch on or off the lighting device 200 that is not powered up, and accordingly decide to apply power to the lighting device 200.

When the user chooses to increase brightness of the lighting device 200, the input unit 200 generates a brightness increase signal. On the other hand, when the user chooses to decrease the brightness of the lighting device 200, the input unit 200 generates a brightness decrease signal. That is, the input unit 220 may directly receive user input.

The memory 240 may include non-volatile memory, such as one or more magnetic disk storage devices, flash memory devices, and/or other non-volatile solid state memory devices. Embodiments are not limited to these examples, and the memory 240 may include a readable storage medium.

For example, the memory 240 may include EEP-ROM (Electronically Erasable and Programmable Read Only Memory). Information can be written to or erased from EEP-ROM by the controller 280 during operation of the controller 280. EEP-ROM may be a memory device that keeps the information stored in it without erasing it even when power is lost.

The memory 240 may store data and commands for operating the lighting device 200.

The memory 240 may store preset PIN (Personal Identification Number) information of the terminal 100 which is used for communications security.

The indication unit 250 may externally indicate whether a communication connection is made (or not made) between the lighting device 200 and the terminal 100. The indication unit 250 may externally indicate whether a communication connection is currently made between the lighting device 200 and the terminal 100 or not, in order to prevent an attempt for connection to other additional terminals 100 from making control of the lighting device 200 complicated and disturbing the user settings for lighting.

The indication unit 250 may include a speaker or bulb for outputting indicator sound upon establishing a communication connection with the terminal 100, and externally indicate whether a communication connection is established (or not).

The drive unit 260 may receive a control signal from the controller 280. The drive unit 260 may apply driving current to the light emitting unit 270 in response to the control signal. The illumination, dimming, color temperature, color, and flickering of light emitted from the light emitting unit 270 are controlled according to the driving current applied from the drive unit 260.

The light emitting unit 270 includes a substrate and at least one light emitting element mounted on the substrate. The light emitting element may emit light when powered, and its brightness may vary with the amount of power applied. The color temperature of the light emitting element may vary with power, and the color of emitted light may vary from combinations of red (R), green (G), and blue (B). The light emitting unit 270 may include a plurality of LED elements. More specifically, the light emitting unit 270 includes white, red, green, and blue LED elements by reaction with fluorescent materials. The light emitting unit 270 is driven by receiving driving current from the drive unit 260.

The controller 280 receives data from the communication unit 210. The controller 280 controls the light emitting unit 270 based on the received data. That is, the controller 280 transmits a control signal to the drive unit 260 based on lighting control data to control the light emitting unit 270 and adjust lighting properties.

The controller 280 may include a user status determiner 281. The user status determiner 281 may determine the user's status based on physical information about the user received from the communication unit 210 or information about motions of the terminal 100. The physical information may include blood flow, blood pressure, heart rate, pulse rate, and how much the pupil dilates.

For example, if the heart rate or pulse rate of the user is greater than or equal to a first reference value, the terminal 100 is continuously moving, and the user's pupil dilates by a reference value or more, the user status determiner 281 determines that the user is exercising. The first reference value is a set value that is determined from a test.

For example, if the heart rate or pulse rate of the user is less than the first reference value and greater than or equal to a second reference value and the terminal 100 is not continuously moving, the user status determiner 281 determines that the user is taking a rest. The first and second reference values are set values that are determined from a test.

For example, if the heart rate or pulse rate of the user is less than the second reference value, the terminal 100 is not continuously moving, and the user's eyes are closed, the user status determiner 281 determines that the user is sleeping. The second reference value is a set value which is determined from a test.

The controller 280 may transmit a control signal to the drive unit 260 in response to the user status determined by the user status determiner 281.

The controller 280 may transmit a control signal to the drive unit 260 and control at least one of the illumination, dimming, color temperature, color, and flickering of light emitted from the light emitting unit 270.

For example, the controller 280 may adjust the color temperature or color of light by transmitting a control signal to the drive unit 260 and selectively driving the white, red, and blue LEDs included in the light emitting unit 270. In another example, the controller 280 may transmit a control signal to the drive unit 260 to give the dimming effect.

If the user status determiner 281 determines that the user is exercising, the controller 280 checks if the pulse rate of the user received from the communication unit 210 is greater than or equal to a reference pulse rate. The reference pulse rate is a pulse rate at which the risk to the user's health starts to increase. If the received pulse rate is greater than or equal to the reference pulse rate, the controller 280 transmits a control signal to the drive unit 260 to make the light emitted from the light emitting unit 270 flicker. The user can stop exercising when seeing flickers of light, and this prevents the user from exercising hard, posing a health risk to the user.

Alternatively, if the user status determiner 281 determines that the user is taking a rest, the controller 280 transmits a control signal to the drive unit 260 to decrease the color temperature of the light emitted from the light emitting unit 270. In this example, the user can rest comfortably since the color temperature of the light is decreased.

Alternatively, if the user status determiner 281 determines that the user is sleeping, the controller 280 transmits a control signal to the drive unit 260 to dim down the light emitted from the light emitting unit 270 or make the light emitting unit 270 emit no light. In this example, the user can sleep deeply since the light is dimmed down.

The controller 280 may be implemented using at least one of application specific integrated circuits (ASICs), digital signal processors (DSPs), digital signal processing devices (DSPDs), programmable logic devices (PLDs), field programmable gate arrays (FPGSs), processors, controllers, micro-controllers, microprocessors and electrical units for executing other functions.

The power supply 290 (or power supply unit) is connected to a power supply source and supplies electric power to the lighting device. The power supply 290 may include a converter that converts between AC and DC depending on the type of power used. The power supply 290 may further include a power conservation circuit or a voltage step-down regulator for supplying a certain level of static current.

If a plurality of terminals 100 are positioned in proximity to the lighting device 200, this may cause a problem with the communication connection between the lighting device 200 and the terminals 100. When the lighting device 200 and the terminal 100 are connected for communication, there may be a problem with an attempt to connect to other additional terminals 100.

In this example, the controller 280 may control the communication unit 210 to form a communication channel with the first terminal 100a with a highest priority according to the order of connection requests made. That is, the communication unit 210 forms a communication channel with the first terminal 100a that has made the earliest connection attempt, among the plurality of terminals 100 that have sent and received a connection signal to and from the lighting device 200. The communication channel is formed without entering a pin code, which simplifies formation of a communication channel by the lighting device, requires less time, and offers convenience for use.

When a communication channel with the first terminal 100a is established, the controller 280 may control the communication unit 210 not to respond to a connection signal from other terminals 100b. Accordingly, this prevents a connection between the lighting device 200 and the plurality of terminals 100a and 100b from making the control of the light emitting unit 270 complicated and prevents other people from changing the user settings.

The communication unit 210 may also form a plurality of communication channels with other terminals 100b simultaneously in response to a connection signal after forming a communication channel with the first terminal 100a.

When the communication unit 210 receives a connection signal from a plurality of wearable devices, the controller 280 may receive pin codes from the plurality of terminals 100, compares them with the PIN (Personal Identification Number) codes stored in the memory 240, and control the communication unit 210 to form a communication channel with the first terminal 100a which is given the highest priority, among the terminals 100 having a matching PIN code. In this example, the PIN codes of the communication unit 210 and priorities of connection of the terminals 100 may be stored in the memory 240.

More specifically, the controller 280 controls the communication unit 210 to transmit a PIN code request signal to the plurality of terminals 100 that have sent a connection signal. Afterwards, the controller 280 may compare the pin codes transmitted from the plurality of the terminals 100 with the PIN codes stored in the memory 240 and determines the priorities of the terminals 100 having a matching PIN code.

Accordingly, the lighting device 200 forms a communication channel with the first terminal 100a with the highest priority. The communication unit 210 does not respond to any terminal having no matching PIN code.

This type of communication channel formation requires a PIN code when forming a communication channel, and therefore has the advantage of preventing the light emitting unit from being controlled by other wearable devices connected without permission.

Figure 3:
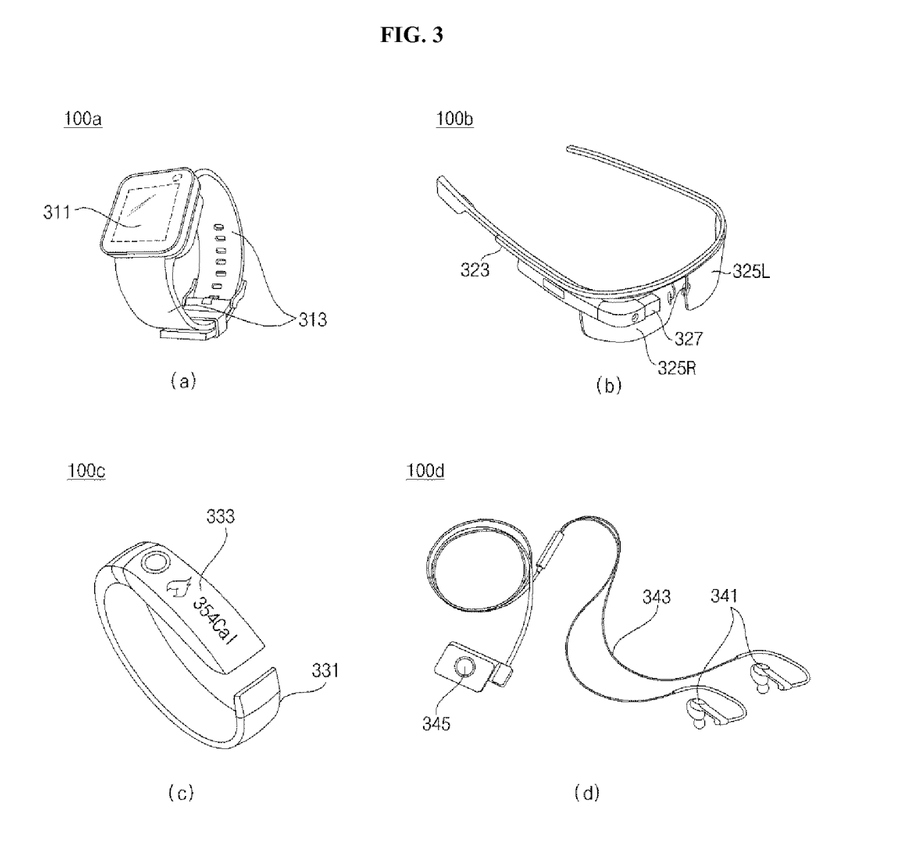
FIG. 3 is a view showing a terminal according to an exemplary embodiment.

FIG. 3 is a view showing a terminal according to an exemplary embodiment. Other embodiments and configurations may also be provided.

This embodiment may be described assuming that the terminal 100 is a wearable device, but embodiments are not limited to this assumption.

The wearable device 200 may be in the form of a watch 100a, glasses 100b, a band 100c, or an earphone 100d.

Referring to FIG. 3(a), a watch-type wearable device (hereinafter referred to as smartwatch) 100a can be worn on the user's wrist.

The smartwatch 100a may include a main body 311 and a band portion 313. The main body 311 may be provided in the form of a round or rectangular case, and the case may incorporate various kinds of electronic units.

The band portion 313 may include a first band portion and a second band portion, and the first and second band portions are connected or disconnected by a fastening device. A display, a sound output module, a camera, and/or a microphone may be arranged on the front side of the main body 311.

With a touchpad overlaid in a layered manner, the display may be configured to operate as a touch screen that enables input of information by a user's touch.

The sound output module may be implemented in the form of a receiver or speaker. The camera may be implemented in a form suitable for capturing images or videos of the user, etc. The microphone may be implemented in a form suitable for receiving the voice of the user and other sounds. The microphone may convert an audio signal input from the user into an electrical signal and outputs it.

An interface and a power supply may be arranged on the rear side of the main body 311.

The interface may be used as a channel through which data is exchanged with external devices. The power supply may act as a battery for supplying power to the smartwatch 100a and may be detachably attached to the main body 311 for charging.

A user input unit and an antenna may be arranged on the side of the main body 311.

The user input unit can employ any method so long as they can be manipulated in a tactile manner. The user input unit may be implemented as a dome switch or a touch pad that allows the user to input commands or information by pushing or touching it, or as a wheel, jog, or joystick that is manipulated by turning the keys.

The antenna includes an antenna for calling and a broadcast signal receiving antenna, and may be installed in such a way that it is retractable from the main body 311.

The band portion 313 is connected to the main body 311 and acts to secure the smartwatch 100a to the user's wrist. The band portion 313 may be made of, but not limited to, rubber, metal, ceramics, leather, or urethane.

The band portion 313 may include a touchpad for receiving commands or information by the user's touch. The touchpad may be implemented in areas of a given length of the first and second band portions from the point of connection to the main body 311.

The smartwatch 100a may include the sensing unit 130, as discussed with reference to FIG. 2.

As described above, the motion sensor 132 included in the smartwatch 100a may include a location sensor or an acceleration sensor. The smartwatch 100a may measure an amount of exercise and calories the user burns by means of the location sensor or the acceleration sensor. That is, when the user is wearing the smartwatch 100a and moving the arm wearing it, the smartwatch 100a can measure the amount of exercise and calories the user burns by means of the motion sensor 132.

The smartwatch 100a may include the optical sensor 133. In this example, the optical sensor 133 can sense the blood flow in the user's arm or a change in skin transparency with heartbeat. The smartwatch 100a can measure the heart rate, blood pressure, etc. of the user using the sensed blood flow or the sensed amount of change in skin transparency with heart rate.

Referring to FIG. 3(b), a glasses-type wearable device (hereinafter referred to as smartglasses) 100b can be worn on the user's head for use.

The smartglasses 100b may include a frame 323, glasses 325L and 325R, and a display 327. The internal space of the frame 323 constituting the glasses incorporates various kinds of electronic units.

A sound output module, a camera, a microphone, an interface, and/or a power supply may be arranged on the frame 323.

The sound output module may be implemented in the form of a receiver or speaker. The camera may be implemented in a form suitable for capturing images or videos of the user, etc. The microphone may be implemented in a form suitable for receiving the voice of the user and other sounds. The microphone converts an audio signal input from the user into an electrical signal and outputs it.

The interface may be used as a channel through which data is exchanged with external devices. The power supply may act as a battery for supplying power to the smartglasses 100b and may be detachably attached to the frame 323 for charging.

The glasses 325L and 325R and the display 327 may be mounted on the frame 323.

The glasses 325 may include a left-eye glass 325L and a right-eye glass 325R. The left-eye glass 325L and the right-eye glass 325R may transmit light. This may allow the user wearing the smartglasses 100b to see an external object with the naked eye. That is, the user can recognize a real object transmitted through the glasses 325L and 325R.

The smartglasses 100b may include the sensing unit 130, as disclosed with reference to FIG. 2.

The smartglasses 100b may include the optical sensor 133. The optical sensor 133 may be arranged to sense the user's eye. In this example, the optical sensor 133 can sense how much the user's pupil dilates. The optical sensor 133 can sense whether the user's eyes are closed or not.

Referring to FIG. 3(c), a band-type wearable device (hereinafter referred to as smartband) 100c can be worn on the user's arm for use.

The smartband 100c may include a main body 331 including a band portion and a display 333.

The main body 331 may incorporate various kinds of electronic units. A sound output module, a camera, a microphone, an interface, and/or a power supply may be arranged on the main body 331.

The sound output module may be implemented in the form of a receiver or speaker. The camera may be implemented in a form suitable for capturing images or videos of the user, etc. The microphone may be implemented in a form suitable for receiving the voice of the user and other sounds. The microphone converts an audio signal input from the user into an electrical signal and outputs it.

The interface may be used as a channel through which data is exchanged with external devices. The power supply may act as a battery for supplying power to the smartband 100c and may be detachably attached to the main body 331 for charging.

With a touchpad overlaid in a layered manner, the display 333 may be configured to operate as a touch screen that enables the input of information by user's touch.

The smartband 100c may include the sensing unit 130, as described with reference to FIG. 2.

As described above, the motion sensor 132 included in the smartband 100c may include a location sensor or an acceleration sensor. The smartband 100c may measure the amount of exercise and calories the user burns by means of the location sensor or the acceleration sensor. That is, when the user is wearing the smartband 100c and moving the arm wearing it, the smartband 100c can measure the amount of exercise and calories the user burns by means of the motion sensor 132.

When the user moves the arm wearing the smartband 100c while the smartband 100c is powered off, the user's motions can be sensed by the motion sensor 132 and the smartband 100c can be powered on.

The smartband 100c may include the optical sensor 133. In this example, the optical sensor 133 can sense the blood flow in the user's arm or a change in skin transparency with heartbeat. The smartband 100c can measure the heart rate, blood pressure, etc. of the user using the sensed blood flow or the sensed amount of change in skin transparency with heart rate.

Referring to FIG. 3(d), an earphone-type wearable device (hereinafter referred to as smart earphones) 100d can be worn on the user's ear for use.

The smart earphones 100d may include a main body 345, a cable 343, and a wearing unit 341. The main body 345 and the wearing unit 341 incorporate various kinds of electronic units.

A manipulation module, a microphone, an interface, and/or a power supply may be arranged on the main body 331.

The manipulation module may act to generate a control signal for controlling operation of the terminal 100 in response to user input and convert the generated control signal into an electrical signal and provide it to the mobile terminal.

The microphone may be implemented in a form suitable for receiving the voice of the user and other sounds. The microphone may convert an audio signal input from the user into an electrical signal and outputs it. The microphone may be arranged on the cable 343.

The interface may be used as a channel through which data is exchanged with external devices. The power supply may act as a battery for supplying power to the smart earphones 100d and may be detachably attached to the main body 331 for charging.

The cable 343 may electrically connect the main body 345 and the wearing unit 341.

The wearing unit 341 may be worn on both ears. The wearing unit 341 may include a sound output module and an optical sensor.

The sound output module may be implemented in the form of a receiver or speaker. The sound output module may convert an electrical signal applied from the mobile terminal 100 into an audio signal and output it. Accordingly, the user can listen to voice signals of the person the user is talking to or audio signals from multimedia being played.

The smart earphones 100d may include the sensing unit 130, as described with reference to FIG. 2.

The smart earphones 100d may include the optical sensor 133. In this example, the optical sensor 133 can sense the blood flow in the user's ears or a change in skin transparency with heartbeat. The smart earphones 100d can measure the heart rate, blood pressure, etc. of the user using the sensed blood flow or the sensed amount of change in skin transparency with heart rate.

Figure 4:
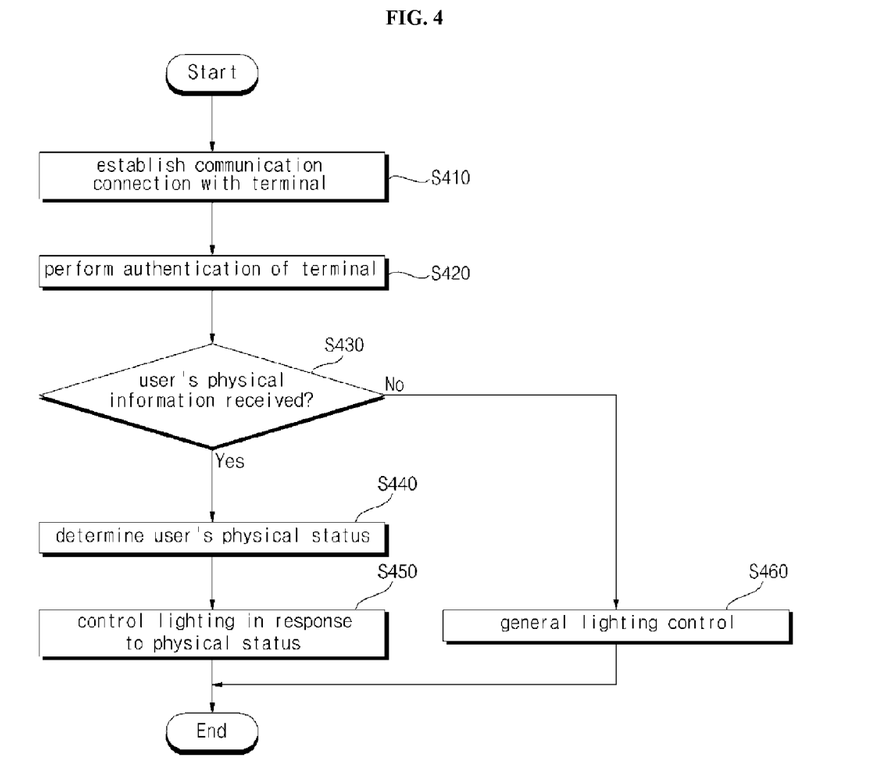
FIG. 4 is a flowchart illustrating operation of the lighting system according to a first exemplary embodiment.

FIG. 4 is a flowchart illustrating operation of the lighting system according to a first exemplary embodiment. Other embodiments and configurations may also be provided.

Referring to FIG. 4, the controller 280 establishes a communication connection with the terminal 100 (S410). Communication with the terminal 100 can be performed using Bluetooth for example. The controller 280 may use communication protocols such as Wi-Fi Direct, RFID (Radio Frequency Identification), IrDA (Infrared Data Association), UWB (Ultra Wideband), ZigBee, and NFC (Near Field Communication), as well as Bluetooth.

While connected to the terminal 100 for communication, the controller 280 may perform authentication of the terminal 100 (S420). If a plurality of terminals 100 are positioned in proximity to the lighting device 200, this may cause a problem with the communication connection between the lighting device 200 and the plurality of terminals 100. Additionally, when the lighting device 200 and the terminal 100 are connected for communication, there may be a problem with an attempt to connect to other terminals 100.

In this example, the controller 280 may control the communication unit 210 to form a communication channel with the first terminal 100a with a highest priority according to an order of connection requests made. That is, the communication unit 210 may form a communication channel with the first terminal 100a that has made an earliest connection attempt, from among the plurality of terminals 100 that have sent and received a connection signal to and from the lighting device 200. The communication channel may be formed without entering a pin code, which simplifies formation of a communication channel by the lighting device, requires less time, and/or offers convenience for use.

When a communication channel with the first terminal 100a is established, the controller 280 may control the communication unit 210 to not respond to a connection signal from other terminals 100b. Accordingly, this may prevent a connection between the lighting device 200 and the plurality of terminals 100a and 100b from making control of the light emitting unit 270 complicated and prevent other people from changing the user settings.

The communication unit 210 may also form a plurality of communication channels with other terminals 100b simultaneously in response to a connection signal after forming a communication channel with the first terminal 100a.

When the communication unit 210 receives a connection signal from a plurality of wearable devices, the controller 280 may receive pin codes from the plurality of terminals 100, compare them with the PIN (Personal Identification Number) codes stored in the memory 240, and control the communication unit 210 to form a communication channel with the first terminal 100a that is given the highest priority, from among the terminals 100 having a matching PIN code. In this example, the PIN codes of the communication unit 210 and priorities of connection of the terminals 100 may be stored in the memory 240.

More specifically, the controller 280 may control the communication unit 210 to transmit a PIN code request signal to the plurality of terminals 100 that have sent a connection signal. Afterwards, the controller 280 may compare the pin codes transmitted from the plurality of the terminals 100 with the PIN codes stored in the memory 240 and determine priorities of the terminals 100 having a matching PIN code.

Accordingly, the lighting device 200 may form a communication channel with the first terminal 100a with the highest priority. The communication unit 210 does not respond to any terminal having no matching PIN code.

This type of communication channel formation may require a PIN code when forming a communication channel, and therefore has an advantage of preventing the light emitting unit from being controlled by other wearable devices connected without permission.

Once authentication of the terminal 100 is completed, the controller 280 may receive, from the terminal 100, physical information about the user or information about motions of the terminal 100 (S430). The physical information about the user may include blood flow, blood pressure, heart rate, pulse rate, and how much the pupil dilates. The physical information about the user or the information about motions of the terminal 100 may be based on information sensed by the sensing unit 130 (of the terminal 100).

Upon receiving, from the terminal 100, the physical information about the user or information about motions of the terminal 100, the controller 280 may determine the user's physical status (S440).

For example, if the heart rate or pulse rate of the user is greater than or equal to a first reference value, the terminal 100 is continuously moving, and the user's pupil dilates by a reference value or more, then the user status determiner 281 determines that the user is exercising. The first reference value may be a set value that is determined from a test.

For example, if the heart rate or pulse rate of the user is less than the first reference value and greater than or equal to a second reference value and the terminal 100 is not continuously moving, then the user status determiner 281 may determine that the user is taking a rest. The first and second reference values are set values that are determined from a test.

For example, if the heart rate or pulse rate of the user is less than the second reference value, the terminal 100 may not be continuously moving, and the user's eyes are closed, then the user status determiner 281 determines that the user is sleeping. The second reference value is a set value that is determined from a test.

Once determination of the user's physical status is completed, the controller 280 may control lighting in response to the user's physical status (S450).

The controller 280 may transmit a control signal to the drive unit 260 and control at least one of the illumination, dimming, color temperature, color, and/or flickering of light emitted from the light emitting unit 270.

For example, the controller 280 may adjust a color temperature of color of light by transmitting a control signal to the drive unit 260 and selectively driving the white, red, and blue LEDs included in the light emitting unit 270. In another example, the controller 280 may transmit a control signal to the drive unit 260 to give the dimming effect.

If the user status determiner 281 determines that the user is exercising, the controller 280 may check or determine if the pulse rate of the user received from the communication unit 210 is greater than or equal to a reference pulse rate. The reference pulse rate is a pulse rate at which the risk to the user's health starts to increase. If the received pulse rate is greater than or equal to the reference pulse rate, the controller 280 transmits a control signal to the drive unit 260 to make the light emitted from the light emitting unit 270 flicker. The user can stop exercising when seeing flickers of light, and this may prevent the user from exercising hard, posing a health risk to the user.

Alternatively, if the user status determiner 281 determines that the user is taking a rest, the controller 280 may transmit a control signal to the drive unit 260 to decrease color temperature of the light emitted from the light emitting unit 270. In this example, the user can rest comfortably since the color temperature of the light is decreased.

Alternatively, if the user status determiner 281 determines that the user is sleeping, the controller 280 may transmit a control signal to the drive unit 260 to dim down the light emitted from the light emitting unit 270 or make the light emitting unit 270 emit no light. In this example, the user can sleep deeply since the light is dimmed down.

If the physical information about the user or the information about the motions of the terminal 100 is not received from the terminal 100 (in operation S430), the controller 280 controls lighting in a general way (S460).

Figure 5:
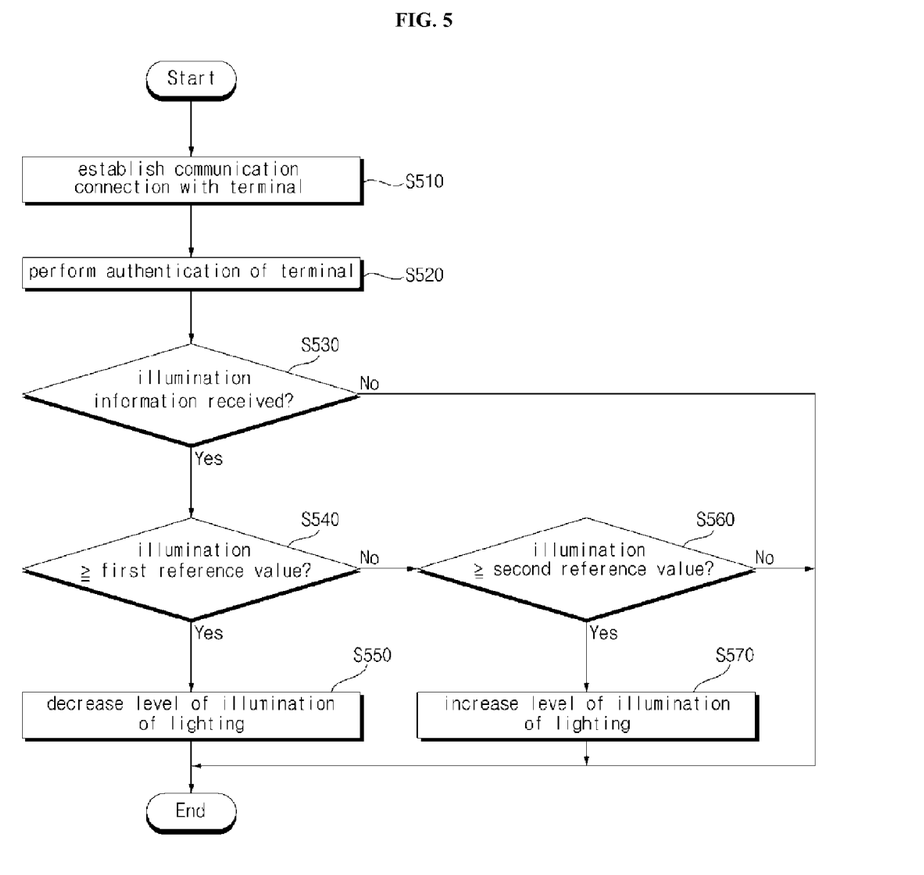
FIG. 5 is a flowchart illustrating operation of the lighting system according to a second exemplary embodiment.

FIG. 5 is a flowchart illustrating operation of the lighting system according to a second exemplary embodiment. Other embodiments and configurations may also be provided.

Referring to FIG. 5, the controller 280 may establish a communication connection with the terminal 100 (S510). A detailed description of operation S510 is identical to operation S410, which is provided with reference to FIG. 4, so redundant description may be omitted.

While connected to the terminal 100 for communication, the controller 280 may perform authentication of the terminal 100 (S520). A detailed description of operation S520 is identical to operation S420 which is given with reference to FIG. 4, so redundant description may be omitted.

Once authentication of the terminal 100 is completed, the controller 280 may receive illumination information from the terminal 100 (S530). The terminal 100 may include the illumination sensor 131. The controller 280 may receive illumination information from the terminal 100 via the communication unit 210.

Having received illumination information from the terminal 100, the controller 280 may determine if the level of illumination is greater than or equal to a first reference value (S540).

If the level of illumination received from the terminal 100 is greater than or equal to the first reference value, the controller 280 may apply a control signal to the drive unit 260 to decrease the level of illumination from the light emitting unit 270 (S550). The first reference value is a set value that is determined by the user's setting.

If the level of illumination received from the terminal 100 is not greater than or equal to the first reference value in operation S540, the controller 280 may determine if the level of illumination is less than or equal to a second reference value (S560).

If the level of illumination received from the terminal 100 is less than or equal to the second reference value, the controller 280 may apply a control signal to the drive unit 260 to increase the level of illumination from the light emitting unit 270 (S570). The second reference value is a set value that is determined by the user's setting.

Figure 6:
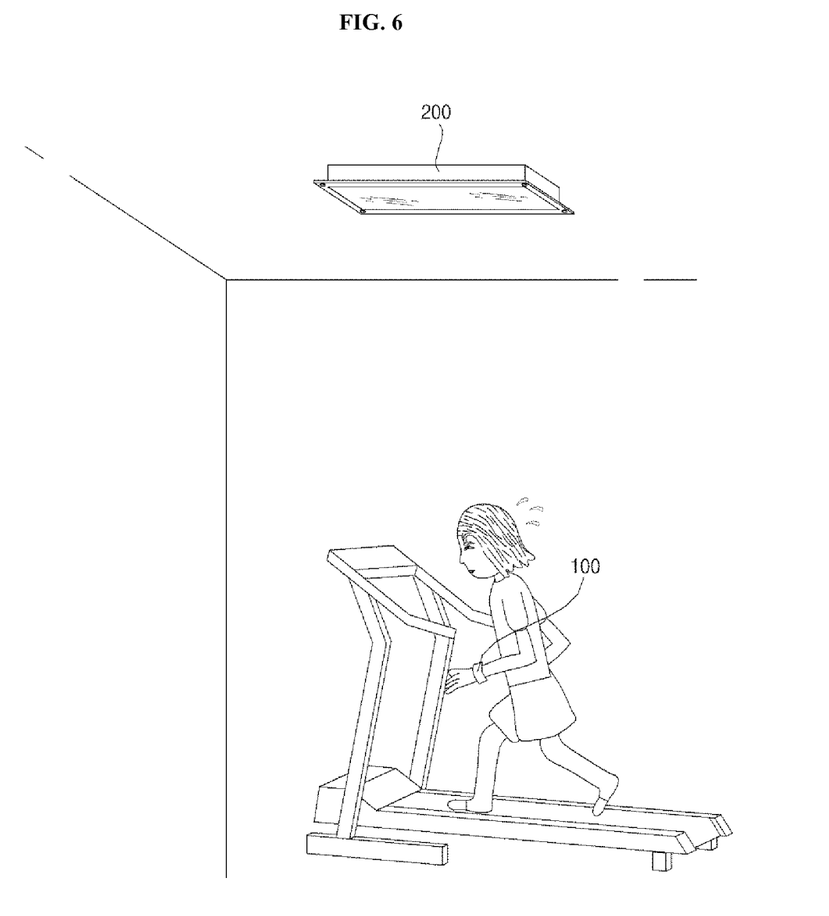
FIGS. 6 to 8 are illustrations of use of a lighting system according to an exemplary embodiment.
Figure 7:
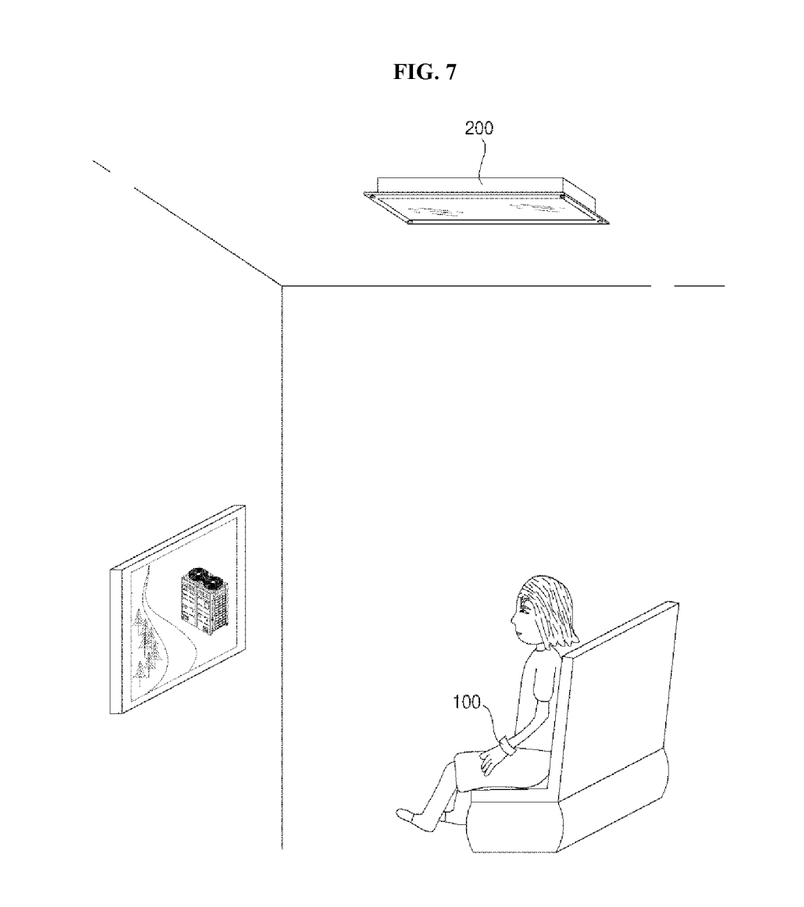
Figure 8:
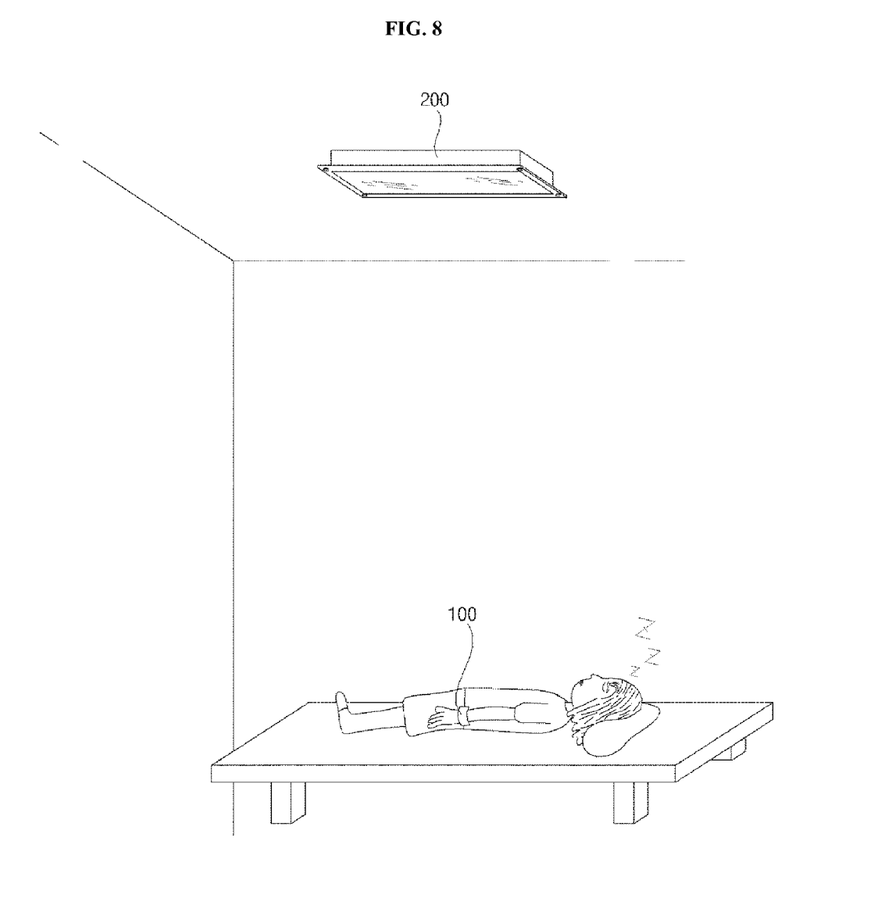

FIGS. 6 to 8 are illustrations of use of a lighting system according to an exemplary embodiment. Other embodiments and configurations may also be provided.

Referring to FIG. 6, the user is exercising wearing the terminal 100 in a place where the lighting device 200 is installed. The sensing unit 130 (included in the terminal 100) may include the motion sensor 132 or the optical sensor 133 for sensing at least one of the following: information in the terminal 100, information on the environment surrounding the terminal 100, and user information.

The motion sensor 132 may sense a motion of the terminal 100. The terminal 100 can determine the user's motion based on the sensed motion of the terminal 100. The optical sensor 133 can sense blood flow in the user's body or a change in skin transparency with heartbeat. The terminal 100 can measure the heart rate or pulse rate of the user using the sensed blood flow or the sensed amount of change in skin transparency with heartbeat.

If the heart rate or pulse rate of the user is greater than or equal to a first reference value, the terminal 100 is continuously moving, and the user's pupil dilates by a reference value or more, then the controller 280 may determine that the user is exercising. The first reference value is a set value that is determined from a test.

If the controller 280 determines that the user is exercising, the controller 280 checks if the pulse rate of the user received from the communication unit 210 is greater than or equal to a reference pulse rate. The reference pulse rate is a pulse rate at which the risk to the user's health starts to increase. If the received pulse rate is greater than or equal to the reference pulse rate, the controller 280 may transmit a control signal to the drive unit 260 to make the light emitted from the light emitting unit 270 flicker. The user can stop exercising when seeing flickers of light, and this may prevent the user from exercising hard, posing a health risk to the user.

Referring to FIG. 7, the user may be taking a rest wearing the terminal 100 in a place where the lighting device 200 is installed. The sensing unit 130 (included in the terminal 100) may include the motion sensor 132 or the optical sensor 133 for sensing at least one of the following: information in the terminal 100, information on the environment surrounding the terminal 100, and user information.

The motion sensor 132 may sense a motion of the terminal 100. The terminal 100 can determine the user's motion based on the sensed motion of the terminal 100. The optical sensor 133 can sense the blood flow in the user's body or a change in skin transparency with heart rate. The terminal 100 can measure the heart rate, blood pressure, etc. of the user using the sensed blood flow or the sensed amount of change in skin transparency with heart rate.

If the heart rate or pulse rate of the user is less than the first reference value and greater than or equal to a second reference value and the terminal 100 is not continuously moving, then the user status determiner 281 may determine that the user is taking a rest. The first and second reference values are set values that are determined from a test.

If the user status determiner 281 determines that the user is taking a rest, then the controller 280 transmits a control signal to the drive unit 260 to decrease the color temperature of the light emitted from the light emitting unit 270. In this example, the user can rest comfortably since the color temperature of the light is decreased.

Referring to FIG. 8, the user is taking a rest wearing the terminal 100 in a place where the lighting device 200 is installed. The sensing unit 130 (included in the terminal 100) may include the motion sensor 132 or the optical sensor 133 for sensing at least one of the following: information in the terminal 100, information on the environment surrounding the terminal 100, and user information.

The motion sensor 132 may sense a motion of the terminal 100. The terminal 100 can determine the user's motion based on the sensed motion of the terminal 100. The optical sensor 133 can sense the blood flow in the user's body or a change in skin transparency with heart rate. The terminal 100 can measure the heart rate, blood pressure, etc. of the user using the sensed blood flow or the sensed amount of change in skin transparency with heart rate. If the terminal 100 is a glasses-type device configured to be worn on a human head, the optical sensor 133 can sense how much the user's pupil dilates. The optical sensor 133 may sense whether the user's eyes are closed or not.

If the heart rate or pulse rate of the user is less than the second reference value, the terminal 100 is not continuously moving, and the user's eyes are closed, then the user status determiner 281 may determine that the user is sleeping. The second reference value is a set value that is determined from a test.

If the user status determiner 281 determines that the user is sleeping, the controller 280 transmits a control signal to the drive unit 260 to dim down the light emitted from the light emitting unit 270 or make the light emitting unit 270 emit no light. In this example, the user can sleep deeply since the light is dimmed down.

Embodiments may be implemented in processor-readable codes in a processor-readable recording medium provided on the SCA-based application system. The processor-readable recording medium includes all kinds of recording devices for storing processor-readable data. Examples of the processor-readable recording medium include a computer-readable storage medium such as ROM, RAM, a CD-ROM, magnetic tapes, floppy disks, and optical data storage devices, and a means implemented in the form of carrier waves, for example, transmission via the Internet. The processor-readable recording medium may be distributed among computer systems connected to a network, and processor-readable codes may be stored and executed in a decentralized fashion.

Furthermore, although the exemplary embodiments have been shown and described, embodiments are not limited to the above specific embodiments, and a person having ordinary skill in the art to which the invention belongs may modify the embodiments in various ways without deuniting from the gist which is written in the claims. The modified embodiments should not be interpreted individually from the technical spirit or prospect of the present invention.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to affect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A lighting device comprising:
    a communication unit to establish a communication connection with a terminal having a sensing unit to sense physical information regarding a user, and the communication unit to receive the physical information from the terminal;
    an input unit to receive user input;
    a light emitting unit that includes one or more light emitting elements; and
    a controller to receive the physical information from the communication unit and to control the light emitting unit based on the received physical information,
    wherein the controller includes a user status determiner to determine the user's status based on the received physical information,
    wherein upon receiving, from the terminal, the physical information, the controller controls the light emitting unit in response to the user's status determined by the user status determiner and the controller controls at least one of dimming, color temperature, and flickering of light from the light emitting unit,
    wherein upon not receiving, from the terminal, the physical information regarding the user, the controller controls the light emitting unit based on the user input from the input unit.

2. The lighting device of claim 1, wherein the physical information corresponds to at least one of the following: blood flow, blood pressure, heart rate, pulse rate, and pupil dilation information.

3. The lighting device of claim 1, wherein the physical information corresponds to heart rate or pulse rate of the user, and
    in response to the user status determiner determining that the user is exercising and the heart rate or the pulse rate is greater than or equal to a reference heart rate or a reference pulse rate, the controller controls the light emitting unit to flicker the light.

4. The lighting device of claim 1, wherein in response to the user status determiner determining that the user is resting, the controller decreases a color temperature of the light from the light emitting unit.

5. The lighting device of claim 1, wherein in response to the user status determiner determining that the user is sleeping, the controller controls the light emitting unit to dim the light or to not emit light.

6. The lighting device of claim 1, wherein the terminal is a wearable device for the user's body.

7. The lighting device of claim 1, further comprising an indication unit to indicate whether a communication connection is established with the terminal.

8. The lighting device of claim 1, further comprising a memory to store a unique code of the terminal,
    wherein when an input code matches the stored unique code, the controller enables data transmission and data reception with the terminal.

9. A lighting system comprising:
    a terminal that includes a sensing unit to sense physical information regarding a user, a wireless communication unit to establish a communication connection with a lighting device, and a terminal controller to control transmission of the physical information from the sensing unit to the lighting device via the wireless communication unit; and
    the lighting device that includes a communication unit to establish a communication connection with the terminal, an input unit to receive user input, a light emitting unit that includes one or more light emitting units, and a controller to receive the physical information from the communication unit and to control the light emitting unit based on the physical information,
    wherein the controller includes a user status determiner to determine the user's status based on the received physical information,
    wherein upon receiving, from the terminal, the physical information, the controller controls the light emitting unit based on the user's status determined by the user status determiner, and the controller controls at least one of dimming, color temperature, and flickering of light from the light emitting unit, in response to the user's status,
    wherein upon not receiving, from the terminal, the physical information regarding the user, the controller controls the light emitting unit based on the user input from the input unit.

10. The lighting system of claim 9, wherein the physical information corresponds to at least one of the following: blood flow, blood pressure, heart rate, pulse rate, and pupil dilation information.

11. The lighting system of claim 9, wherein the terminal is a wearable device for the user's body.

12. The lighting device of claim 1, further comprising a memory configured to store a plurality of PIN codes of the terminals and priorities of connection of the terminals,
    wherein the controller is configured to:

compare transmitted PIN codes from the plurality of the terminals with the PIN codes stored in the memory, form a communication channel with a first terminal with a highest priority based on the priorities stored in the memory, receive the physical information from the first terminal via the wireless communication unit, and control the light emitting unit based on the physical information.

13. The lighting system of claim 9, wherein the lighting device includes a memory configured to store a plurality of PIN codes of the terminals and priorities of connection of the terminals, wherein the controller is configured to:

compare transmitted PIN codes from the plurality of the terminals with the PIN codes stored in the memory, form a communication channel with a first terminal with a highest priority based on the priorities stored in the memory, receive the physical information from the first terminal via the wireless communication unit, and control the light emitting unit based on the physical information.

* * * * *